United States Patent
Nagasaki et al.

(10) Patent No.: US 10,398,803 B2
(45) Date of Patent: *Sep. 3, 2019

(54) NITROXYLRADICAL-CONTAINING COPOLYMER WHICH HAS PHOSPHORIC ACID RESIDUE, AND THE USE OF THE SAME

(71) Applicant: UNIVERSITY OF TSUKUBA, Ibaraki (JP)

(72) Inventors: Yukio Nagasaki, Ibaraki (JP); Yutaka Ikeda, Ibaraki (JP); Kouya Akasaka, Ibaraki (JP)

(73) Assignee: UNIVERSITY OF TSUKUBA, Ibaraki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/779,654

(22) PCT Filed: Nov. 29, 2016

(86) PCT No.: PCT/JP2016/085266
§ 371 (c)(1),
(2) Date: May 29, 2018

(87) PCT Pub. No.: WO2017/094691
PCT Pub. Date: Jun. 8, 2017

(65) Prior Publication Data
US 2018/0256782 A1    Sep. 13, 2018

(30) Foreign Application Priority Data
Nov. 30, 2015    (JP) .................................. 2015-234005

(51) Int. Cl.
*A61L 27/34*    (2006.01)
*A61L 31/10*    (2006.01)
(Continued)

(52) U.S. Cl.
CPC ............... *A61L 27/34* (2013.01); *A61L 31/10* (2013.01); *A61L 33/064* (2013.01); *C08F 8/12* (2013.01);
(Continued)

(58) Field of Classification Search
CPC ............... A23L 1/30; A61K 47/48176; A61K 47/48215; A61K 49/085; A61K 49/126;
(Continued)

(56) References Cited

U.S. PATENT DOCUMENTS 9,962,469 B2 * 5/2018 Nagasaki .............. A61L 31/041
2011/0142787 A1    6/2011 Nagasaki et al.
(Continued)

FOREIGN PATENT DOCUMENTS

EP    2 896 398    7/2015
JP    2011-78706    4/2011
(Continued)

OTHER PUBLICATIONS

Nagasaki et al., "Design of Novel Anti-oxidative Nanomedicine for Ischemia-reperfusion Injury", Drug Delivery System, 30(4):327-335 (2015), with English Abstract.
(Continued)

*Primary Examiner* — Shane Fang
(74) *Attorney, Agent, or Firm* — Wenderoth, Lind & Ponack, L.L.P.

(57) ABSTRACT

Provided is a coating agent which can be stably immobilized on metal surface, and which can give blood compatibility. Provided is a copolymer which is usable as the above-mentioned coating agent that comprises PEG segment and a segment which has a phosphoric acid residue (PO(—OH)$_2$) and a cyclic nitroxideradical randomly as a side chain or a pendant group.

8 Claims, 4 Drawing Sheets

(51) Int. Cl.
  *C08F 8/30* (2006.01)
  *C08F 8/40* (2006.01)
  *C08G 81/02* (2006.01)
  *C08L 25/18* (2006.01)
  *C09D 125/02* (2006.01)
  *A61L 33/06* (2006.01)
  *C08F 8/12* (2006.01)
  *C08F 8/26* (2006.01)
  *C08F 8/32* (2006.01)
  *C08F 293/00* (2006.01)
  *C09D 153/00* (2006.01)
  *C08G 65/334* (2006.01)
  *C08G 65/337* (2006.01)
  *C09D 171/02* (2006.01)
  *C08F 12/14* (2006.01)

(52) U.S. Cl.
  CPC .............. *C08F 8/26* (2013.01); *C08F 8/30* (2013.01); *C08F 8/32* (2013.01); *C08F 8/40* (2013.01); *C08F 293/005* (2013.01); *C08G 65/334* (2013.01); *C08G 65/337* (2013.01); *C08G 81/025* (2013.01); *C08L 25/18* (2013.01); *C09D 125/02* (2013.01); *C09D 153/005* (2013.01); *C09D 171/02* (2013.01); *C08F 12/14* (2013.01); *C08F 2438/03* (2013.01); *C08L 2203/02* (2013.01); *C08L 2203/16* (2013.01)

(58) Field of Classification Search
  CPC ............ A61K 49/1806; A61K 49/1824; A61K 49/20; C08F 297/00; C08F 8/30; C08G 65/33396; C08G 65/334; C08G 65/3344; C08G 73/1071; C08L 25/04; C08L 71/02
  See application file for complete search history.

(56) References Cited

U.S. PATENT DOCUMENTS

2012/0273460 A1    11/2012   Kang et al.
2016/0346438 A1*   12/2016   Nagasaki .............. A61L 31/041

FOREIGN PATENT DOCUMENTS

JP    2011-184429    9/2011
JP    2012-111700    6/2012
JP    2012-233187    11/2012
JP    2013-173689    9/2013
WO    2009/133647    11/2009

OTHER PUBLICATIONS

Yoshitomi et al., "Creation of a blood-compatible surface: A novel strategy for suppressing blood activation and coagulation using a nitroxide radical-containing polymer with reactive oxygen species scavenging activity", Acta Biomaterialia, 8:1323-1329 (2012).

Kamimura et al., "Block ionomer complexes of PEG-block-poly(4-vinylbenzylphosphonate) and cationic surfactants as highly stable, pH responsive drug delivery system", Journal of Controlled Release, 160:486-494 (2012).

International Search Report dated Dec. 27, 2016 in International (PCT) Application No. PCT/JP2016/085266.

Extended European Search Report, dated May 9, 2019 in corresponding European Patent Application No. 16870628.1.

Kamimura et al., "Near-infrared (1550 nm) in vivo bioimaging based on rare-earth doped ceramic nanophosphors modified with PEG-b-poly(4-vinylbenzyl-phosphonate)", Nanoscale, 3(9): 3705-3713 (2011).

* cited by examiner

[FIG. 1]
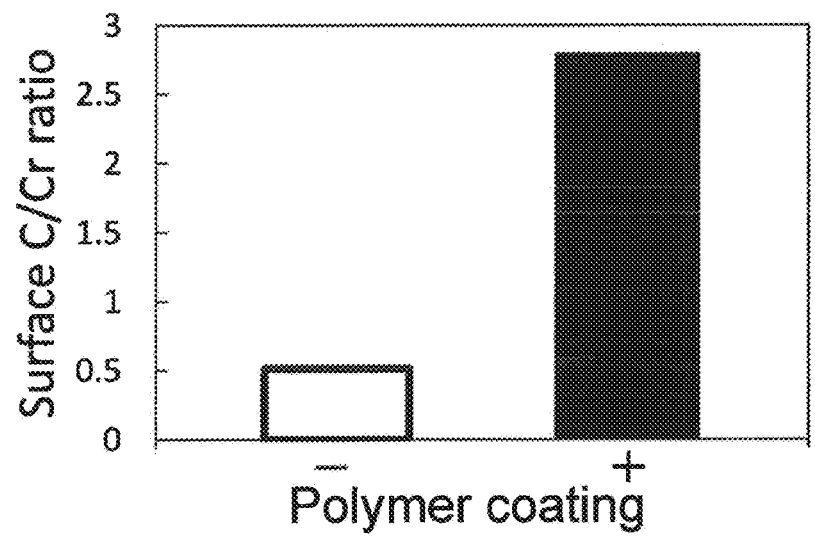
[FIG. 2]
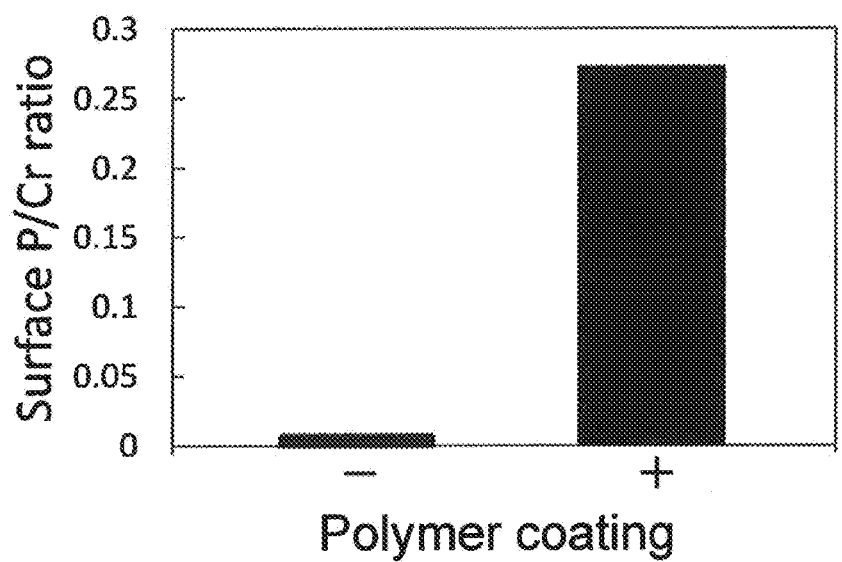

[FIG. 3]
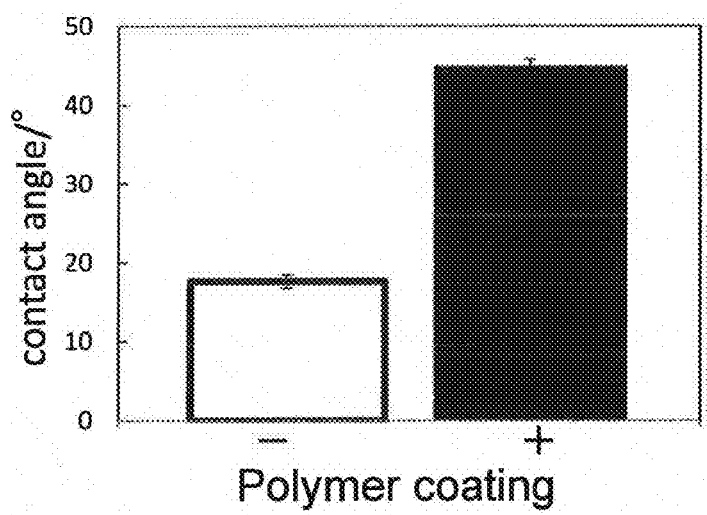
[FIG. 4]
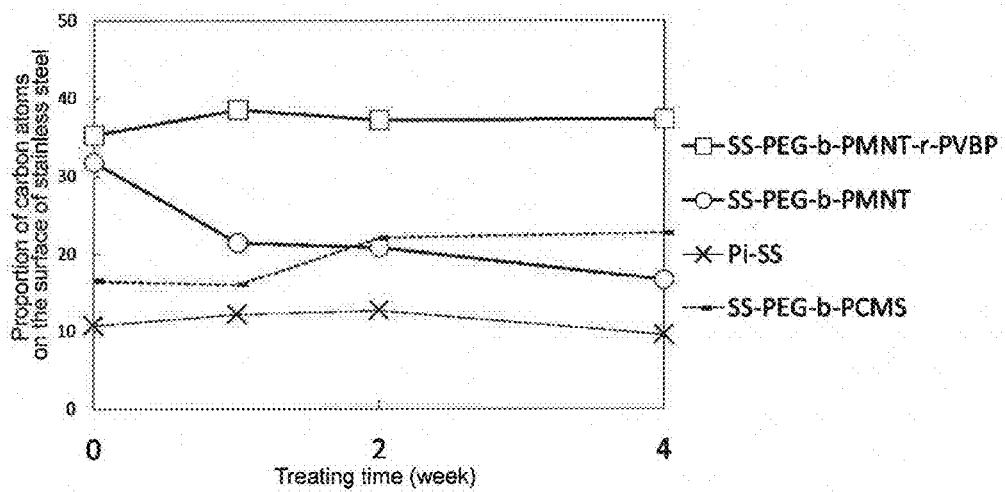

[FIG. 5]
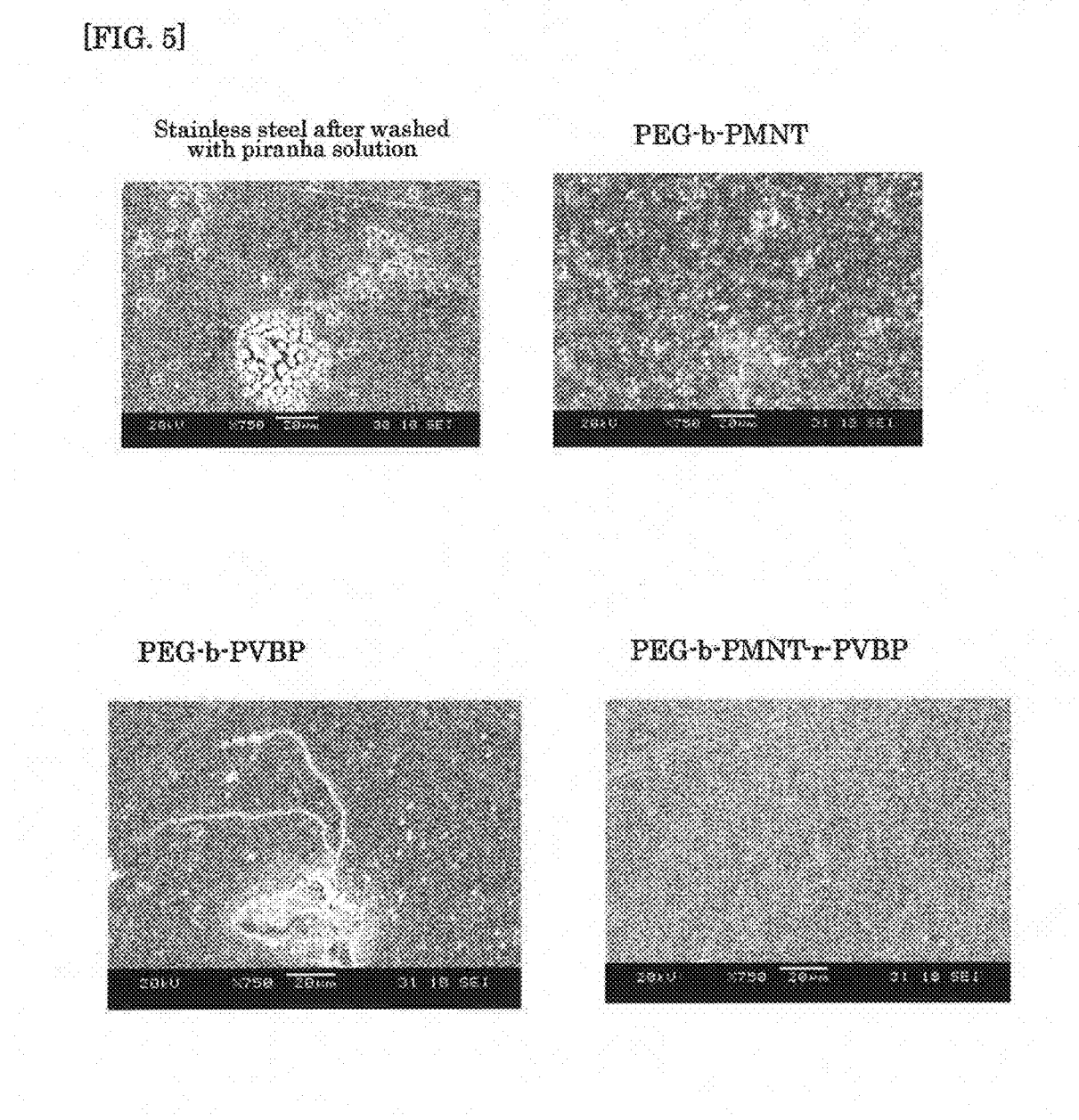

[FIG. 6]
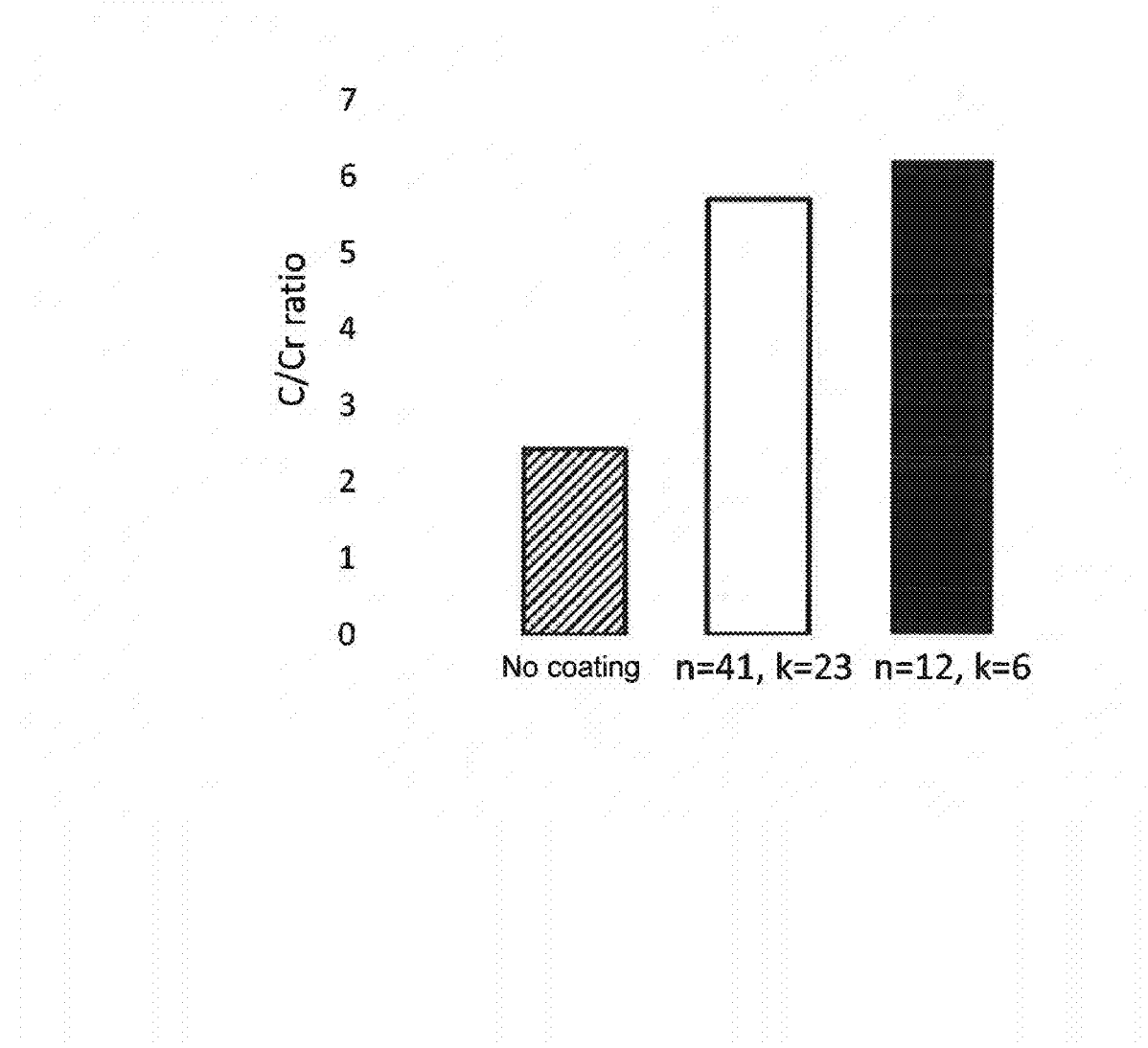

NITROXYLRADICAL-CONTAINING COPOLYMER WHICH HAS PHOSPHORIC ACID RESIDUE, AND THE USE OF THE SAME

TECHNOLOGICAL FIELD

This invention relates to a nitroxylradical-containing copolymer which has phosphoric acid residue, more specifically to a copolymer which comprises polyethylene glycol) segment (hereinafter sometimes abbreviated as PEG) and a segment which has randomly a phosphoric acid residue and a cyclic nitroxideradical in each pendant group. This invention further relates to the use of said copolymer for the sake of modification of metal surface, or specifically for the sake of changing a metal material into a material having biocompatibility such as antithrombotic material.

BACKGROUND ART

Metal material is now being widely used in the field of medical treatment. For instance, stainless steel is used for stent, and titanium particles are used for joints of artificial heart. Although these metal materials are mechanically strong and are handleable, they have a grave defect that, when brought into contact with blood, they activate blood to cause thrombus. Therefore serious side effects like cerebral infarction have been sometimes brought about. Hence, various studies have been made to develop medical technique by which to process the surface of these metal materials, to prevent coagulation reaction which occurs owing to the activation of blood, and to thus give antithrombotic properties to metal materials. Fundamental solution has however yet to be achieved.

Paying attention to the fact that active oxygen plays an important role in the activation of blood, the inventors of this invention have so far reported that a polymer which has nitroxylradical which gets rid of active oxygen, when applied to living body, can be used for the treatment of various species of inflammation or the like (Patent Document 1), or that said polymer can be used for the improvement of biocompatibility of a surface which gets in contact with substance which is originated from living body (Patent Document 2). They have also reported that polystyrene beads coated with said polymer inhibit the activation of blood (Non-patent Document 1). Furthermore, the inventors of this invention have developed a technique by which to coat a metal surface with polymer having phosphoric acid residue (Non-patent Document 2).

There has been a demand in medical field for the development of a new material for stent or the like which has antithrombotic properties. In response, there has been developed medical agent-eluting stents which have on their surface a medical agent having antithrombotic properties. There are reports, however, that these stents are more likely to cause thrombus to some patients as compared with conventional stents. Long period effects of those stents are yet to be verified. It is expected therefore that a metal material which maintains mechanical advantages and can also give antithrombotic properties would be able to be applied not only to stent but also to other devices made of metal.

PRIOR ART DOCUMENTS

Patent Documents

Patent Document 1: WO 2009/133647 or US 2011/0142787 A1
Patent Document 2: Official Gazette of JP 2011-78706 A

Non-Patent Documents

Non-patent Document 1: Acta Biomater. 2012 March; 8(3): 1323-9
Non-patent Document 2: J Control Release 2012 Jun. 28: 160(3): 486-94

SUMMARY OF INVENTION

Problem which this Invention Intends to Solve

Under the above-mentioned circumstances, it is considered to be necessary to develop a surface modifier which is usable in the field of medical techniques, that has affinity to metals, while keeping mechanical advantages of metal material and maintaining ability to inhibit blood activation.

Means to Solve the Problem

The inventors have now found that a block copolymer which comprises a PEG segment and a segment which has a cyclic nitroxideradical in pendant group, wherein some cyclic nitroxideradicals in the repeating unit of the latter segment are randomly replaced with phosphoric acid residues (—PO(—OH)$_2$) is usable as a surface modifier which can solve the above-mentioned problem.

Thus, this invention provides a copolymer of the following formula (I):

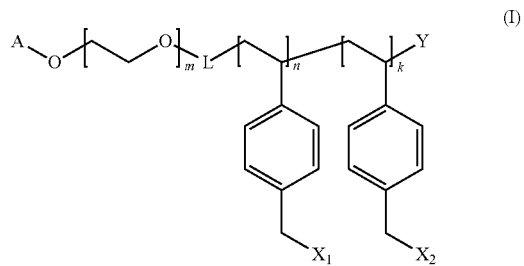

wherein A denotes a hydrogen atom, an unsubstituted or substituted C$_{1-12}$ alkyl, wherein, when the alkyl is substituted, the substituent is a formyl group or an R$_1$R$_2$CH— group wherein R$_1$ and R$_2$ independently denote C$_{1-4}$ alkoxy or denote, when put together, —OCH$_2$CH$_2$O—, —O(CH$_2$)$_3$O— or —O(CH$_2$)$_4$O—; L denotes a bond or a linker which is selected from the group consisting of the following formulae:

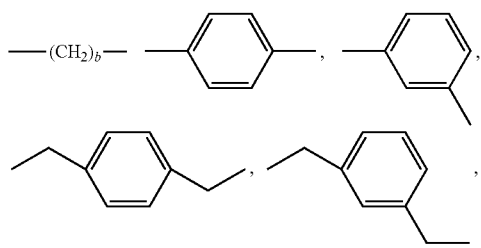

—(CH$_2$)$_c$S—, —CO(CH$_2$)$_c$S—, —(CH$_2$)$_c$NH—, —(CH$_2$)$_c$CO—, —CO—, —COO—, and —CONH—; X$_1$ is selected from the groups, covalently bonded via —$(CH_2)_a$— —NH—$(CH_2)_a$— or —$(CH_2)_a$—O—$(CH_2)_a$—, of formulae:

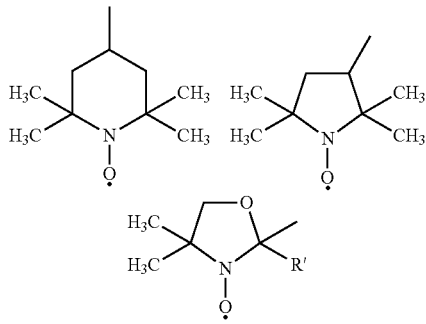

$X_2$ denotes PO(—OH)$_2$; Y denotes H, SH or S—C(=S)-Ph wherein Ph denotes a phenyl which may be substituted by one or two methyl or methoxy groups; a independently denotes an integer of 0 to 5; b denotes an integer of 2 to 6; c denotes an integer of 1 to 5; m is an integer of 2 to 10,000; n is an integer of 1 to 360; k is an integer of 1 to 480; provided that up to 50%, preferably up to 20%, more desirably up to 10%, in n $X_1$'s and up to 50%, preferably up to 20%, more desirably up to 10%, in k $X_2$'s may be H, halogen or hydroxyl, although it is most desirable that 100% of $X_1$ and $X_2$ are as defined above; and provided that n units in the corresponding repeating units and k units in the corresponding repeating units are randomly present.

In preferable embodiments of copolymer, n+k is an integer of 5 to 600, n/(n+k) is 0.2 to 0.8, preferably 0.4 to 0.7, k/(n+k) is 0.2 to 0.8, preferably 0.4 to 0.6, wherein, in principle, 100% of n and k repeating units are groups as defined above with respect to $X_1$ and $X_2$, in the definitions of n and k of the above-mentioned formula.

As another embodiment, this invention provides a surface of metal material which supports the above-mentioned copolymer.

As another embodiment, this invention provides a device which has on its surface a coating film originated from the above-mentioned copolymer, wherein said surface is selected from the surface of metal material of stent, auxiliary artificial heart, artificial joint, cell culturing device, cell analyzing device and cell separating device and the parts thereof.

Effects of Invention

The above-mentioned copolymer of this invention is stably kept as a coating film on the surface of metal material, in particular of product which is directly or indirectly in contact with human body fluid, tissue or organ. This copolymer can inhibit for instance blood activation or the like, and has therefore a function to give biocompatibility to the surface of metal material of stent, auxiliary artificial heart, artificial joint, cell culturing device, cell analyzing device and cell separating device and the parts thereof.

BRIEF EXPLANATION OF FIGURES

FIG. 1 A graph to show the result (C/Cr ratio) of analysis of surface elements (with respect to carbon atom) by XPS of the surface of stainless steel which is prepared by polymer coating of a stainless steel with Compound (7) (13-18) which is obtained in Production Example 6 and of stainless steel before said coating (after washed with piranha solution).

FIG. 2 A graph to show the result (P/Cr ratio) of analysis of surface elements (with respect to phosphorus atom) by XPS of the same.

FIG. 3 A graph to show the result of measurement of contact angle of the surface of stainless steel which has been polymer-coated with Compound (7) (13-18).

FIG. 4 A graph to show the result of evaluation of stability of polymer coat under phosphate buffered saline.

FIG. 5 Photos to show the result of SEM measurement of the surface (control) of stainless steel, not coated with polymer, after whole blood contact test, and of the surface of polymer-coated stainless steel after whole blood contact test (including Comparative Example).

FIG. 6 A graph to show the result of analysis by XPS of Compound (7) (12-6) (corresponding to n=12, k=6 in the figure) and Compound (7) (41-23) (corresponding to n=41, k=23 in the figure) on the basis of the coating of Examples 2 and 3.

DETAILED DESCRIPTION OF INVENTION

On the copolymer of formula (I):

The $C_{1-12}$ alkyl of the present invention is an alkyl having 1 to 12 carbon atoms which may be straight or branched, and includes, not restrictively, methyl, ethyl, propyl, isopropyl, n-butyl, tert-butyl, hexyl, heptyl, octyl, nonyl, undecyl, dodecyl, etc.

In the definitions of variable groups or parts in formula (I), linker L is combined with the directivity as mentioned unless otherwise defined. For instance, in case of the group —$(CH_2)_c$S— which has directivity, the carbon atom of methylene group is bound with oxygen atom of ethylene oxy, and the sulfur atom is bound with the carbon atom of main methylene group in any one of the unit either of the n repeating units each of which has $X_1$ as a pendant group or of the k repeating units each of which has $X_2$ as a pendant group. As would be understood from the above definitions or explanation, n units in the corresponding repeating units and k units in the corresponding repeating units are randomly present. In other words, any one of n units in the corresponding repeating units or any one of k units in the corresponding repeating units is bound with L, and one or more of the other units of repeating units are randomly bound with the unit which is bound with L.

In this invention, bond or binding means covalent bond unless otherwise defined. The above-explained linker L is preferably paraxylylene or methaxylylene in view of advantages in production or stability or the like of the above-mentioned copolymer.

The group —$(CH_2)_a$—NH—$(CH_2)_a$— or —$(CH_2)_a$—O—$(CH_2)_a$— which binds $X_1$ with the paraxylylene part of the pendant group is preferably —NH— or —O— where a denotes 0 (zero) from the viewpoint of production, but this is not restrictive. $X_2$ denotes a phosphoric acid residue PO(—OH)$_2$. The copolymer of formula (I) is supposed to be immobilized to a metal material surface via these phosphoric acid residues.

Y denotes H, SH or S—C(=S)-Ph, wherein Ph denotes a phenyl which may be substituted by one or two methyl or methoxy groups. Nevertheless, Ph is preferably unsubstituted.

In the definitions of n and k of formula (I), n and k are preferably of plural number, and are more desirably at least 4 and 3, respectively. In said definitions, n+k is an integer of 5 to 600, preferably 10 to 500, more desirably 20 to 300, wherein n/(n+k) is 0.2 to 0.8, and k/(n+k) is 0.2 to 0.8. Preferably n/(n+k) is 0.4 to 0.7, and k/(n+k) is preferably 0.4 to 0.6. In principle, 100% of n and k repeating units are as defined above (i.e., other than H, halogen and hydroxyl which are mentioned in the provision) with respect to $X_1$ and $X_2$. In addition, for the desired purpose of this invention of giving high affinity with respect to metals while maintaining ability to inhibit blood activation, n is at least 6, preferably at least 8, more desirably at least 11, and k is at least 3, preferably at least 6, more desirably at least 8.

The mark m denotes an integer generally in the range of 2 to 10,000, preferably 20 to 5,000, more desirably 20 to 3,000, although not restricted with regard to theoretically optimum range.

Although not restricted, the copolymer of formula (I) can be produced from precursor block copolymer of the following formula (P):

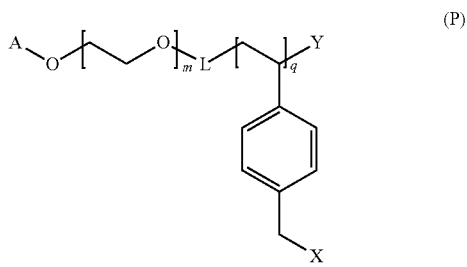

wherein A, L, Y and m are as defined above, X denotes halogen (chlorine, bromine, iodine), and q corresponds to the above-mentioned integer of n+k, by a method of converting the group X into $X_1$ and $X_2$.

A part of the block copolymer of formula (P) is mentioned in the above-mentioned Patent Document 1, or can be produced by the production method which is shown in the same, or can be produced on the basis of Production Example which is mentioned later. In the conversion, the group X may be converted first into $X_1$ and then into $X_2$, or vice versa, whichever is acceptable. Preferably, however, the group X is converted first into $X_2$, since it would easily provide a copolymer which contains phosphoric acid residue at a rate as desired. The conversion reaction is preferably conducted in accordance with the method which is mentioned in Production Example which is mentioned later, although it can also be conducted under publicly known conditions.

On metal material:

Metal material is not restricted so long as the same serves the purpose of this invention. Preferably, however, metal material is material for medical product or product which is used for any other test or research, or parts thereof. Medical product means products which are used for medical activity such as diagnosis, examination and therapy, or products for test or research which are supposed to be used for said activities, or members or parts thereof. They may be used in vivo or in vitro, whichever is acceptable. In particular included are those products which are directly or indirectly in contact with human body fluid, tissue or organ. Although not restrictive, these products are exemplified by stent, auxiliary artificial heart, artificial joint, cell culturing device, cell analyzing device and cell separating device. Among these products or parts thereof, those in which the above-mentioned contact surface is metal such as stainless steel, titanium and titanium alloy are intended as objects to which this invention is to be applied.

The above-mentioned copolymer is supported or maintained on said surface by any publicly known coating method by use of a solution of the copolymer. In this invention, when an article thus coated by any method or a coating film is subjected to the removal of solvent and drying, the copolymer is immobilized to metal surface with certain peeling resistance, and is thus supported or maintained thereon.

On the surface of metal material on which the copolymer of this invention is thus supported or maintained, a coating film made from the copolymer is stably immobilized on said surface, giving biocompatibility to the metal surface.

EXAMPLES

Concrete examples of this invention are explained below, although they are not intended to restrict this invention.

Preferable method to produce the copolymer of this invention is summarized by the following reaction schemes. Each step for the production is concretely explained later along the line of these reaction schemes.

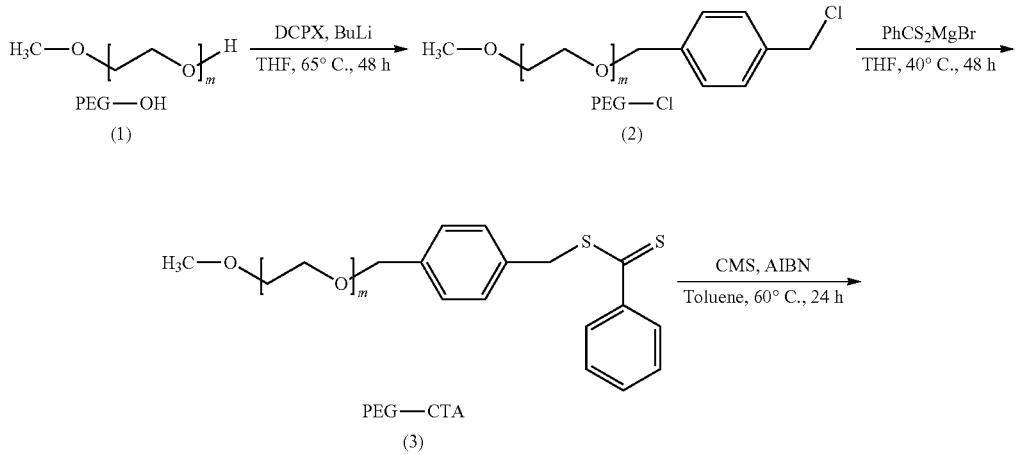

-continued
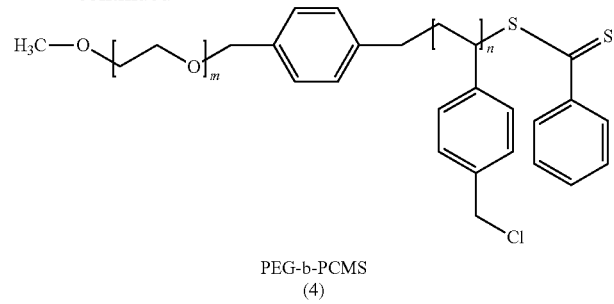
PEG-b-PCMS
(4)
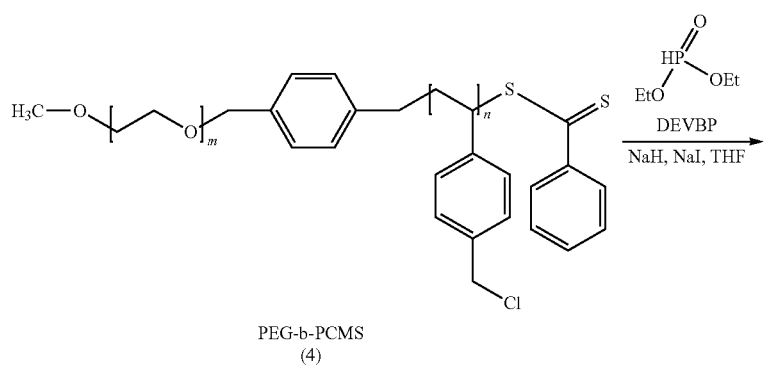
PEG-b-PCMS
(4)
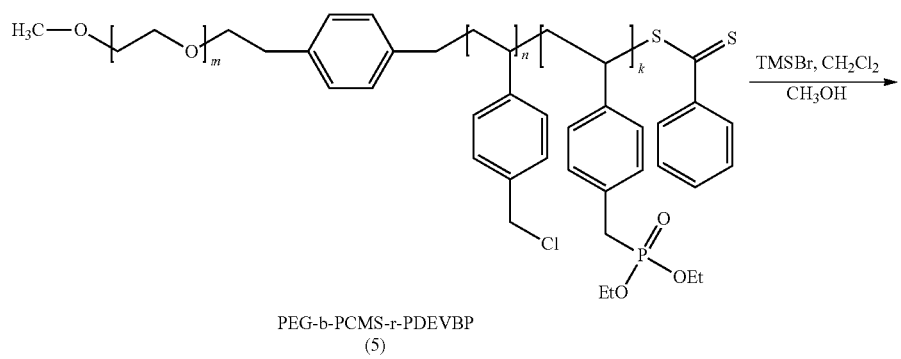
PEG-b-PCMS-r-PDEVBP
(5)
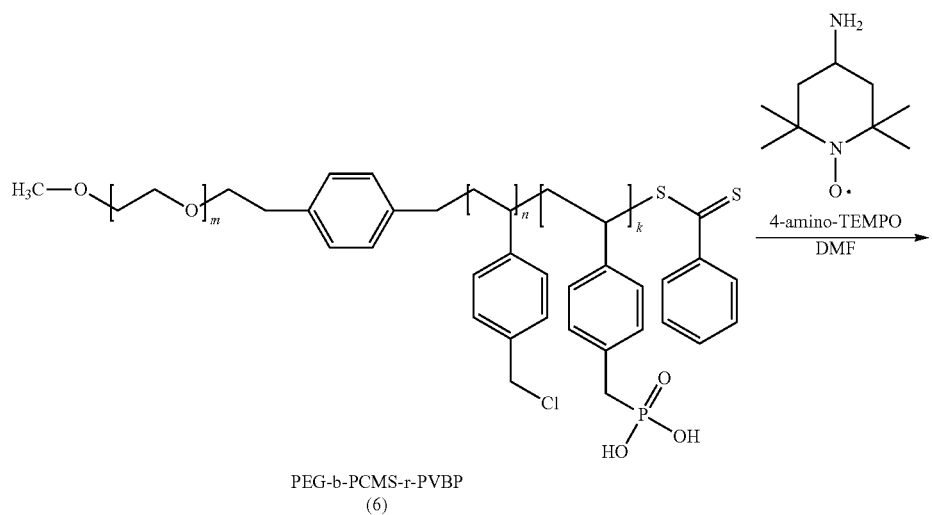
PEG-b-PCMS-r-PVBP
(6)

-continued

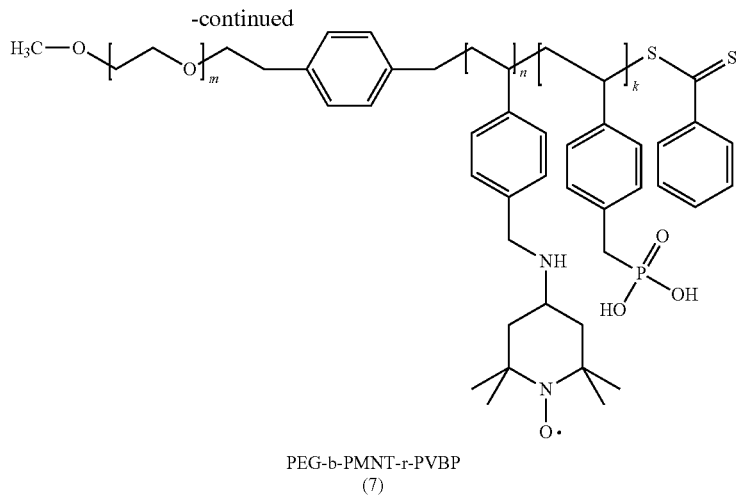

PEG-b-PMNT-r-PVBP
(7)

Production Example 1

Synthesis of PEG-Cl (2)

PEG-OH (1) (50 g; molecular weight: 5,000; 0.01 mol) was put into a 500 ml eggplant flask, and was dried for 24 hours under reduced pressure at 110° C. After the temperature was lowered to 65° C., distilled tetrahydrofuran (THF) solvent (200 ml), n-butyl lithium (16 mmol, 10 ml), α,α-dichloro-p-xylene (DCPX) (25 g, 0.14 mol) were added with nitrogen purge, and the resulting mixture was stirred for 48 hours at 65° C. After the reaction was over, the mixture was subjected to reprecipitation with 2-propanol (IPA) which had been cooled in a freezer. Reaction product was separated by centrifugation, and supernatant was removed. The reaction product was dissolved in methanol, and was subjected to reprecipitation again. Reprecipitation was repeated nine times. After the ninth centrifugation and removal of supernatant, the reaction product was dried under reduced pressure in a desiccator for 36 hours. After the drying under reduced pressure was over, the above-captioned compound (2) was obtained at a yield of 80%.

$^1$HNMR (CDCl$_3$, 400 MHz) 7.35-7.34 ppm (q, 4H), 4.58 ppm (s, 2H), 4.56 ppm (s, 2H), 3.83-3.45 ppm (s, 474H), 3.38 ppm (s, 3H)

Production Example 2

Synthesis of PEG-CTA (3)

The above-mentioned compound (2) (40 g; 0.08 mol) was put into a 500 ml eggplant flask, and was dried overnight under reduced pressure at 110° C. Apart from the same, distilled tetrahydrofuran (THF) solvent (50 ml), carbon disulfide (0.07 mol, 4 ml), phenylmagnesium bromide (6.7 ml, 3M, 0.02 mol) were put into a 100 ml eggplant flask with nitrogen purge under cooling with ice water bathing, and the resulting mixture was stirred for 20 minutes. Reaction was allowed to continue for two hours at room temperature to give Grignard reagent. After compound (2) was cooled down to 40° C., distilled tetrahydrofuran (THF) solvent (200 ml) and Grignard reagent were added with nitrogen purge, and the resulting mixture was allowed to react for 48 hours at 40° C. After the reaction was over, the mixture was subjected to reprecipitation with 2-propanol (IPA) which had been cooled in a freezer. Reaction product was separated by centrifugation, and supernatant was removed. The reaction product was dissolved in methanol, and was subjected to reprecipitation again. Reprecipitation was repeated five times. After the fifth centrifugation and removal of supernatant, the reaction product was dried under reduced pressure in a desiccator for 36 hours. After the drying under reduced pressure was over, the above-captioned compound (3) was obtained at a yield of 95%.

$^1$HNMR (CDCl$_3$, 400 MHz) 8.00 ppm (d, 1H), 7.98 ppm (d, 1H), 7.54-7.50 ppm (t, 1H), 7.40-7.30 ppm (m, 6H), 4.58 ppm (s, 2H), 4.55 ppm (s, 2H), 3.83-3.45 ppm (s, 500H), 3.38 ppm (s, 3H)

GPC Mw: 5231 Mw/Mn=1.21

Production Example 3

Synthesis of PEG-b-PCMS (4) (13-18)

Compound (3) (4 g; 0.8 mmol) obtained in Production Example 2 and azobisisobutyronitrile (24 mg, 0.14 mmol) were put into a 100 ml eggplant flask, and a three-way stopcock was attached. Distilled toluene (40 ml) and p-chloromethyl styrene (16.4 ml, 0.12 mol) were added with nitrogen purge, and the resulting mixture was subjected to polymerization reaction for 24 hours at 60° C. After the reaction was over, the mixture was subjected to reprecipitation with 600 ml of diethyl ether. Reaction product was separated by suction filtration, and filtrate was removed. The reaction product was dissolved in acetone, and was subjected to reprecipitation again. Reprecipitation was repeated three times. After the third filtration, the reaction product was dissolved in 15 ml of benzene, and the resulting solution was freeze-dried. After the freeze-drying was over, the above-captioned compound (4) was obtained at a yield of 78%.

$^1$HNMR (CDCl$_3$, 400 MHz) 7.24-6.16 ppm (m, 152H), 4.67-4.27 ppm (m, 74H), 3.83-3.45 ppm (s, 470H), 3.38 ppm (s, 3H), 2.40-1.06 ppm (m, 126H)

GPC Mw=12465 Mw/Mn=1.35

Production Example 4

Synthesis of PEG-b-PCMS-r-PDEVBP (5) (13-18)

Compound (4) (1.1 g; 0.1 mmol) obtained in Production Example 3 was put into a 100 ml eggplant flask, a three-way stopcock was attached, and 10 ml of distilled tetrahydrofuran (THF) solvent was added. Put into another 100 ml eggplant flask were 55% sodium hydroxide (144 mg, 3.3 mmol) and a small amount of sodium iodide, and a three-way stopcock was attached. With nitrogen purge, 16 ml of distilled tetrahydrofuran (THF) solvent was added, and, subsequently, diethyl phosphite (0.43 ml, 3.3 mmol) was added. The resulting solution was added dropwise to Compound (4) under cooling with ice water bathing, and the resulting mixture was allowed to react at room temperature for 15 hours. After the reaction was over, solvent was removed with an evaporator. The reaction product was dissolved in methanol, and was purified by methanol dialysis for 48 hours with dialysis membrane MWCO 3500. After dialysis was over, solvent was removed with an evaporator. The reaction product was dissolved in 5 ml of benzene, and the resulting solution was freeze-dried. After the freeze-drying was over, the above-captioned compound (5) was obtained at a yield of 96%.

$^1$HNMR (CDCl$_3$, 400 MHz) 7.24-6.16 ppm (m, 137H), 4.67-4.24 ppm (m, 26H), 4.21-3.79 ppm (m, 80H), 3.78-3.45 ppm (s, 423H), 3.38 ppm (s, 3H), 3.23-2.86 ppm (s, 36H), 2.37-0.94 ppm (m, 232H)

$^{31}$PNMR (MeOD, 600 MHz, standard: 85% phosphoric acid) 26.84 ppm

Production Example 5

Synthesis of PEG-b-PCMS-r-PVBP (6) (13-18)

Compound (5) (1 g; 0.1 mmol) obtained in Production Example 4 was put into a 100 ml two-necked eggplant flask, and a three-way stopcock and a reflux condenser were attached. With nitrogen purge, dichloromethane (12 ml) and trimethylsilyl bromide (1.07 ml, 8.2 mmol) were added, and the resulting mixture was allowed to react under reflux for three hours at 45° C. After the reaction was over, solvent was removed with an evaporator. The reaction product was dissolved in an excess amount of methanol, and the resultant solution was allowed to react at room temperature for 24 hours. After the reaction was over, solvent was removed with an evaporator. The reaction product was dissolved in methanol, and the resultant solution was purified by methanol dialysis for 48 hours with dialysis membrane MWCO 3500. After dialysis was over, solvent was removed with an evaporator. The reaction product was dissolved in 5 ml of benzene, and the resulting solution was freeze-dried. After the freeze-drying was over, the above-captioned compound (6) was obtained at a yield of 93%.

$^1$HNMR (D$_2$O, 400 MHz) 7.52-5.63 ppm (br, 160H), 4.52-4.01 ppm (br, 22H), 3.73-3.27 ppm (m, 594H), 3.83-3.20 ppm (s, 3H), 2.90-2.34 ppm (br, 36H), 2.26-0.54 ppm (br, 104H)

$^{31}$PNMR (MeOD, 600 MHz, standard: 85% phosphoric acid) 23.99 ppm

Production Example 6

Synthesis of PEG-b-PMNT-r-PVBP (7) (13-18)

Compound (6) (490 mg; 0.04 mmol) obtained in Production Example 5 was put into a 50 ml eggplant flask, a three-way stopcock was attached, and 5 ml of dimethyl sulfoxide was added. Put into another 50 ml eggplant flask was 4-amino-2,2,6,6-tetramethylpiperidine 1-oxyl free radical (4-amino TEMPO) (445 mg, 2.6 mmol), and a three-way stopcock was attached, and 5 ml of dimethyl sulfoxide was added with nitrogen purge. The resulting 4-amino TEMPO solution was dripped into Compound (6), and the resulting solution was allowed to react at room temperature for 24 hours. After the reaction was over, the resultant solution was purified by methanol dialysis for 48 hours with dialysis membrane MW CO 3500. After dialysis was over, solvent was removed with an evaporator. The reaction product was dissolved in benzene, and the resulting solution was freeze-dried. After the freeze-drying was over, the above-captioned compound (7) was obtained at a yield of 98%.

According to the result of measurement of $^1$HNMR and electron spin resonance (ESR), the number of 4-amino TEMPOxylated units and the number of phosphorylated units (which numbers correspond to n and k of the above formula) in compound (7) were 13 and 18 respectively.

$^1$HNMR (D$_2$O, phenylhydrazine, 400 MHz) 3.69-3.23 ppm (m, 530H), 3.18 ppm (s, 3H), 2.99-2.40 ppm (br, 34H), 1.78-1.59 ppm (s, 37H), 1.09-0.86 ppm (s, 114H)

Production Example 7

Synthesis of PEG-b-PCMS (4) (12-6)

Compound (3) (4.5 g) obtained in Production Example 2 and azobisisobutyronitrile (40 mg) were put into a 100 ml eggplant flask, and a three-way stopcock was attached. Distilled toluene (100 ml) and p-chloromethyl styrene (10 ml) were added with nitrogen purge, and the resulting mixture was subjected to polymerization reaction for 24 hours at 60° C. After the reaction was over, the mixture was subjected to reprecipitation with 600 ml of diethyl ether. Reaction product was separated by suction filtration, and filtrate was removed. The reaction product was dissolved in acetone, and was subjected to reprecipitation again with isopropanol and diethyl ether. After freeze-drying, the above-captioned compound (4) (6.25 g) was obtained.

Production Example 8

Synthesis of PEG-b-PCMS-r-PDEVBP (5) (12-6)

Compound (4) (830 mg) obtained in Production Example 7 was put into a 100 ml eggplant flask, a three-way stopcock was attached, and 8 ml of distilled tetrahydrofuran (THF) solvent was added. Put into another 100 ml eggplant flask were 55% sodium hydroxide (43 mg) and a small amount of sodium iodide, and a three-way stopcock was attached. With nitrogen purge, 3 ml of distilled tetrahydrofuran (THF) solvent was added, and, then, diethyl phosphite (0.13 ml) was added. The resulting solution was added dropwise to Compound (4) under cooling with ice water bathing, and the resulting mixture was allowed to react at room temperature for 15 hours. After the reaction was over, solvent was removed with an evaporator. The reaction product was dissolved in methanol, and was purified by methanol dialysis for 48 hours with dialysis membrane MWCO 3500. After dialysis was over, solvent was removed with an evaporator. The reaction product was dissolved in 5 ml of benzene, and the resulting solution was freeze-dried. After the freeze-drying was over, the above-captioned compound (5) was obtained at a yield of 86%.

Production Example 9

Synthesis of PEG-b-PCMS-r-PVBP (6) (12-6)

Compound (5) (0.086 mmol) obtained in Production Example 8 was put into a 100 ml two-necked eggplant flask, and a three-way stopcock and a reflux condenser were attached. With nitrogen purge, dichloromethane (10 ml) and trimethylsilyl bromide (300 μl, 2.3 mmol) were added, and the resulting mixture was allowed to react under reflux for three hours at 45° C. After the reaction was over, solvent was removed with an evaporator. The reaction product was dissolved in an excess amount of methanol, and the resultant solution was allowed to react at room temperature for 24 hours. After the reaction was over, solvent was removed with an evaporator. The reaction product was dissolved in methanol, and the resultant solution was purified by methanol dialysis for 48 hours with dialysis membrane MWCO 3500. After dialysis was over, solvent was removed with an evaporator. The reaction product was dissolved in 5 ml of benzene, and the resulting solution was freeze-dried. After the freeze-drying was over, the above-captioned compound (6) was obtained at a yield of 65%.

Production Example 10

Synthesis of PEG-b-PMNT-r-PVBP (7) (12-6)

Compound (6) (500 mg) obtained in Production Example 9 was put into a 50 ml eggplant flask, a three-way stopcock was attached, and 5 ml of dimethyl sulfoxide was added. Put into another 50 ml eggplant flask was 4-amino-2,2,6,6-tetramethylpiperidine 1-oxyl free radical (4-amino TEMPO) (616 mg), a three-way stopcock was attached, and 5 ml of dimethyl sulfoxide was added with nitrogen purge. The resulting 4-amino TEMPO solution was dripped into Compound (6), and the resulting solution was allowed to react at room temperature for 24 hours. After the reaction was over, the resultant solution was purified by methanol dialysis for 48 hours with dialysis membrane MWCO 3500. After dialysis was over, solvent was removed with an evaporator. The reaction product was dissolved in benzene, and the resulting solution was freeze-dried. After the freeze-drying was over, the above-captioned compound (7) was obtained at a yield of 91%.

According to the result of measurement of $^1$HNMR and electron spin resonance (ESR), the number of 4-amino TEMPOxylated units and the number of phosphorylated units (which numbers correspond to n and k of the above formula) in compound (7) were 12 and 6 respectively.

Production Example 11

Synthesis of PEG-b-PCMS (4) (41-23)

Compound (3) (4.5 g) Obtained in Production Example 2 and azobisisobutyronitrile (40 mg) were put into a 100 ml eggplant flask, and a three-way stopcock was attached. Distilled toluene (100 ml) and p-chloromethyl styrene (25 ml) were added with nitrogen purge, and the resulting mixture was subjected to polymerization reaction for 24 hours at 60° C. After the reaction was over, the mixture was subjected to reprecipitation with 600 ml of diethyl ether. Reaction product was separated by suction filtration, and filtrate was removed. The reaction product was dissolved in acetone, and was subjected to reprecipitation again with isopropanol and diethyl ether. After freeze-drying, the above-captioned compound (4) was obtained at a yield of 20%.

Production Example 12

Synthesis of PEG-b-PCMS-r-PDEVBP (5) (41-23)

Compound (4) (710 mg) obtained in Production Example 11 was put into a 100 ml eggplant flask, a three-way stopcock was attached, and 10 ml of distilled tetrahydrofuran (THF) solvent was added. Put into another 100 ml eggplant flask were 55% sodium hydroxide (144 mg) and a small amount of sodium iodide, and a three-way stopcock was attached. With nitrogen purge, 16 ml of distilled tetrahydrofuran (THF) solvent was added, and, then, diethyl phosphite (0.43 ml) was added. The resulting solution was added dropwise to Compound (4) under cooling with ice water bathing, and the resulting mixture was allowed to react at room temperature for 15 hours. After the reaction was over, solvent was removed with an evaporator. The reaction product was dissolved in methanol, and was purified by methanol dialysis for 48 hours with dialysis membrane MWCO 3500. After dialysis was over, solvent was removed with an evaporator. The reaction product was dissolved in 5 ml of benzene, and the resulting solution was freeze-dried. After the freeze-drying was over, the above-captioned compound (5) was obtained at a yield of 98%.

Production Example 13

Synthesis of PEG-b-PCMS-r-PVBP (6) (41-23)

Compound (5) (0.042 mmol) obtained in Production Example 12 was put into a 100 ml two-necked eggplant flask, and a three-way stopcock and a reflux condenser were attached. With nitrogen purge, dichloromethane (5 ml) and trimethylsilyl bromide (650 μl, 5.1 mmol) were added, and the resulting mixture was allowed to react under reflux for three hours at 45° C. After the reaction was over, solvent was removed with an evaporator. The reaction product was dissolved in an excess amount of methanol, and the resultant solution was allowed to react at room temperature for 24 hours. After the reaction was over, solvent was removed with an evaporator. The reaction product was dissolved in methanol, and the resultant solution was purified by methanol dialysis for 48 hours with dialysis membrane MWCO 3500. After dialysis was over, solvent was removed with an evaporator. The reaction product was dissolved in 5 ml of benzene, and the resulting solution was freeze-dried. After the freeze-drying was over, the above-captioned compound (6) was obtained at a yield of 90%.

Production Example 14

Synthesis of PEG-b-PMNT-r-PVBP (7) (41-23)

Compound (6) (0.02 mmol) obtained in Production Example 13 was put into a 50 ml eggplant flask, a three-way stopcock was attached, and 5 ml of dimethyl sulfoxide was added. Put into another 50 ml eggplant flask was 4-amino-2,2,6,6-tetramethylpiperidine 1-oxyl free radical (4-amino TEMPO) (1.4 g), a three-way stopcock was attached, and 5 ml of dimethyl sulfoxide was added with nitrogen purge. The resulting 4-amino TEMPO solution was dripped into Compound (6), and the resulting solution was allowed to react at room temperature for 24 hours. After the reaction was over, the resultant solution was purified by methanol dialysis for 48 hours with dialysis membrane MWCO 3500. After dialysis was over, solvent was removed with an evaporator. The reaction product was dissolved in benzene, and the resulting solution was freeze-dried. After the freeze-drying was over, the above-captioned compound (7) was obtained at a yield of 98%.

According to the result of measurement of $^1$HNMR and electron spin resonance (ESR), the number of 4-amino TEMPOxylated units and the number of phosphorylated units (which numbers correspond to n and k of the above formula) in compound (7) were 41 and 23 respectively.

Example 1

Coating (1) Polymer Coating of Stainless Steel

A stainless steel (SUS430) having a thickness of 1 mm was cut into pieces of 1 cm×1 cm, which were subjected to ultrasonic cleaning for 15 minutes with distilled water, methanol and acetone. After cleaning was over, the stainless steel pieces were soaked in piranha solution (sulfuric acid: hydrogen peroxide=3:1) at 60° C. for 10 minutes so that the surface might be cleansed and hydroxylated. Immediately after washed with distilled water, the stainless steel pieces were soaked in a methanol solution of Compound (7) (13-18) (15 mg/ml) for 24 hours, so that the stainless steel pieces might be coated with polymer. After coating, the stainless steel pieces were washed with methanol, dried in nitrogen flow, and, thus, polymer-coated stainless steel was obtained.

(2) Elemental Analysis of Coating Surface by X-Ray Photoelectron Spectroscopy (XPS)

This test is elemental analysis by X-ray Photoelectron Spectroscopy (XPS) (JEOL Ltd., JPS-9010TR) of the surface of polymer-coated stainless steel obtained by the above-mentioned method.

In the measurement of XPS, aluminum (AlKα, hν=1468.6 eV) was used as a source, and spectrum was obtained for each of the elements C, O, Fe, Cr, N and P. From thus obtained spectra, it was found that the proportion of carbon atom (C/Cr) on the surface of polymer-coated stainless steel had increased, as compared with the surface before coated with polymer. The same was found with phosphorus element which is characteristic of the polymer. It was known from these results that the surface of stainless steel had been coated with the polymer. The results of elemental analysis of the surface by XPS are shown by FIGS. 1 and 2. It is seen from these figures that carbon and phosphorus were each detected in large amount from the polymer-coated surface.

(3) Evaluation of Wettability of Surface by the Measurement of Contact Angle

This test evaluated the wettability of the surface of polymer-coated stainless steel which had been obtained by the above-mentioned method, with a contact angle meter (CA-X; Kyowa Interface Science Co., Ltd.). In the measurement of contact angle, a 2 μl drop of distilled water was prepared, and, at the time when 60 seconds had passed, the drop was measured for contact angle as static contact angle of water. Results are shown by FIG. 3. As is seen from the figure, stainless steel washed with piranha solution gave a low contact angle since the surface had been hydroxylated to become hydrophilic. After coated with polymer, the stainless steel surface gave a remarkably increased contact angle. This result is considered to have been brought by the polymer having covered hydroxyl group on the surface and the stainless steel surface having become less hydrophilic than before coated. It is suggested also from the above-mentioned result that the stainless steel surface was coated with the polymer.

(4) Evaluation of the Stability of Polymer in Phosphate Buffered Saline

In this test, polymer-coated stainless steel which had been obtained by the above-mentioned method was soaked in phosphate buffered saline, and the stability of polymer was thereby evaluated. Polymer-coated stainless steel was soaked in PBS (150 mM, 15 ml) at 37° C. for a certain time. Subsequently, the polymer-coated stainless steel was recovered, washed with distilled water, dried in nitrogen flow, and was then subjected to elemental analysis of the surface by XPS. Results are shown by FIG. 4. It is known from the figure that polymer coating was stably maintained on the surface of stainless steel (SS-PEG-b-PMNT-r-PVBP) which had been coated with PEG-b-PMNT-r-PVBP (7) or Compound (7) (13-18) having phosphoric acid residue, since the figure indicates no change in the proportion of carbon atoms (C/Cr) on the surface of said stainless steel after the stainless steel was soaked in PBS for four weeks. Whereas it is known that no polymer coating was maintained on the surface of stainless steel which had been coated with PEG-b-PMNT (which corresponds to Compound (7) wherein k=0) and with PEG-b-PCMS (which corresponds to Compound (6) wherein k=0) each having no phosphoric acid residue, since the figure indicates low proportion of carbon atoms (C/Cr). It is seen from these facts that phosphoric acid residue of the polymer and the surface of stainless steel are chemically bonded stably with each other. Incidentally, "Pi-SS" shows a data of surface where one surface of stainless steel piece had been washed with piranha solution.

(5) Whole Blood Contact Test of Polymer-Coated Stainless Steel

In this test, the polymer-coated stainless steel which had been obtained by the above-mentioned method was brought into contact with whole blood, and the surface of the stainless steel after contact was observed with a scanning electron microscope (SEM) (JSM-5510SEM; JEOL Ltd.). A piece of polymer-coated stainless steel and a stainless steel piece as a control which had been washed with piranha solution were each placed in a 1.5 ml-tube, into which heparin was put in advance so that the proportion of heparin to blood may be 5 U/ml. Whole blood which had been taken from Balb/c mouse was put into the tubes and was, after a three-hour incubation at 37° C., washed with PBS three times. Subsequently, stainless surface was infiltrated with 2% glutaraldehyde overnight for immobilization, and was lastly dehydrated with ethanol (50%, 70% and 100%) and was dried in nitrogen flow, and, thus, samples for SEM were prepared. For the measurement with SEM, gold was sputtered onto the samples with a sputterer (AUTO FINE COATER JFC-1600; JEOL). Results showed the adhesion of blood clots or blood components to the surface of stainless steel before coated with polymer.

Blood clots or blood components were seen to have adhered also to the surface of stainless steel (each Comparative Example) coated with PEG-b-PVBP (which corresponds to Compound (7) wherein n=0). This result means that the above-mentioned polymer cannot fully prevent blood activation or blood coagulation reaction which is caused by the same. Whereas no blood cell components were seen to have adhered to the surface of stainless steel coated with PEG-b-PMNT-r-PVBP (7)(13-18) which has both phosphoric acid residue and nitroxylradical. It was known from these facts that PEG-b-PMNT-r-PVBP suitably gives blood compatibility to stainless steel. FIG. 5 gives photos of results of the above-mentioned measurement with SEM.

Examples 2 and 3

Coating

Coating treatment was conducted under the same conditions as mentioned in Example 1 (1), except that Compound (7) (13-18) was replaced with Compound (7) (12-6) which is obtained in Production Example 10 and with Compound (7) (41-23) which is obtained in Production Example 14. Subsequently, thus coated surfaces were each subjected to elemental analysis (C/Cr) by XPS according to the method of Example 1 (2). Results are shown by FIG. 6.

It is seen from the figure that the copolymer of this invention is stably carried or supported on the surface of stainless steel over the wide range of the number (k) of phosphorylated units. In the figure, the black color column is based on the data of the surface coated with Compound (7) (12-6) (corresponding to n=12, k=6), and the white color column is based on the data of the surface coated with. Compound (7) (41-23) (corresponding to n=41, k=23). The hatched column is based on the data of the surface of stainless steel after washed with piranha solution, and without polymer coating.

The invention claimed is:

1. A copolymer of the following formula (I):

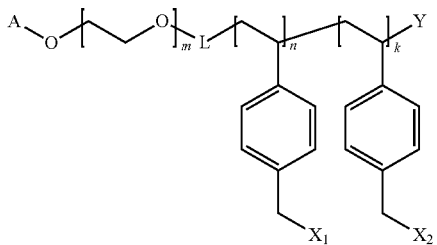
(I)

wherein:

A is a hydrogen atom, an unsubstituted or substituted $C_{1-12}$ alkyl, wherein when the alkyl is substituted, the substituent is a formyl group or a group of the formula $R_1R_2CH-$ wherein $R_1$ and $R_2$ independently represent $C_{1-4}$ alkoxy or when put together, represent $-OCH_2CH_2O-$, $-O(CH_2)_3O-$ or $-O(CH_2)_4O-$;

L is either a bond or a linker selected from the group consisting of the following formulae:

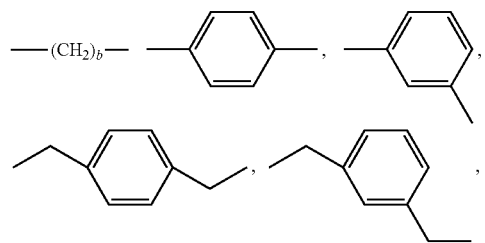

$-(CH_2)_cS-$, $-CO(CH_2)_cS-$, $-(CH_2)_cNH-$, $-(CH_2)_cCO-$, $-CO-$, $-COO-$, and $-CONH-$;

$X_1$ is selected from the group consisting of the following formulae:

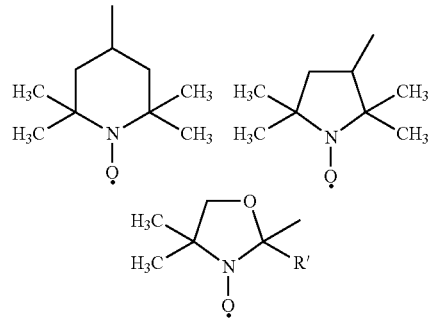

and wherein the formulae are covalently bonded via a group of the formula $-(CH_2)_a-NH-(CH_2)_a-$ or $-(CH_2)_a-O-(CH_2)_a-$;

$X_2$ is $PO(-OH)_2$;

Y is H, SH or $S-C(=S)$-Ph wherein Ph is a phenyl which may be substituted by one or two methyl or methoxy groups;

a's independently are an integer of 0 to 5;

b is an integer of 2 to 6;

c's are an integer of 1 to 5;

m is an integer of 2 to 10,000;

n is an integer of 1 to 360; and k is an integer of 1 to 480;

provided that up to 50% of n X's or up to 50% of k Y's may respectively be H, halogen or hydroxyl; and also provided that n units in the corresponding repeating units and k units in the corresponding repeating units are randomly present.

2. The copolymer of claim 1 wherein n+k is an integer of 5 to 600, n/(n+k) is 0.2 to 0.8, k/(n+k) is 0.2 to 0.8, wherein, in principle, 100% of n and k repeating units are groups as defined above with respect to $X_1$ and $X_2$, in the definitions of n and k of the above-mentioned formula.

3. The copolymer of claim 2 wherein k is an integer of at least 3, and n is an integer of at least 3.

4. The copolymer of claim 1 wherein L is paraxylylene or methaxylylene.

5. A surface of metal material which supports the copolymer of claim 1.

6. The surface of metal material of claim 5 wherein metal material is stainless steel, titanium or titanium alloy.

7. The surface of metal material of claim 5 which is selected from the surface of stent, auxiliary artificial heart, artificial joint, cell culturing device, cell analyzing device and cell separating device or parts thereof.

8. A device which has on its surface a coating film originated from the copolymer of claim 1, wherein said surface is selected from the surface of metal material of stent, auxiliary artificial heart, artificial joint, cell culturing device, cell analyzing device and cell separating device and the parts thereof.

* * * * *